US010106492B2

(12) United States Patent
Bomkamp et al.

(10) Patent No.: US 10,106,492 B2
(45) Date of Patent: Oct. 23, 2018

(54) FLUORINATED CARBONYL COMPOUNDS COMPRISING A TRIPLE BOND, METHODS FOR THEIR MANUFACTURE AND USES THEREOF

(71) Applicant: SOLVAY SA, Brussels (BE)

(72) Inventors: Martin Bomkamp, Hannover (DE); Dirk Seffer, Hannover (DE)

(73) Assignee: SOLVAY SA, Brussels (BE)

(*) Notice: Subject to any disclaimer, the term of this patent is extended or adjusted under 35 U.S.C. 154(b) by 583 days.

(21) Appl. No.: 14/414,583

(22) PCT Filed: Jul. 9, 2013

(86) PCT No.: PCT/EP2013/064504
§ 371 (c)(1),
(2) Date: Jan. 13, 2015

(87) PCT Pub. No.: WO2014/009377
PCT Pub. Date: Jan. 16, 2014

(65) Prior Publication Data
US 2015/0191423 A1  Jul. 9, 2015

(30) Foreign Application Priority Data
Jul. 13, 2012  (EP) ..................... 12176268

(51) Int. Cl.
C07C 255/03 (2006.01)
C07C 69/96 (2006.01)
H01G 11/60 (2013.01)
H01G 11/64 (2013.01)
H01M 10/052 (2010.01)
H01M 10/0567 (2010.01)
H01M 10/0569 (2010.01)
C07C 255/14 (2006.01)
C07C 253/30 (2006.01)
H01G 11/62 (2013.01)
H01M 12/08 (2006.01)

(52) U.S. Cl.
CPC ............ *C07C 255/03* (2013.01); *C07C 69/96* (2013.01); *C07C 253/30* (2013.01); *C07C 255/14* (2013.01); *H01G 11/60* (2013.01); *H01G 11/62* (2013.01); *H01G 11/64* (2013.01); *H01M 10/052* (2013.01); *H01M 10/0567* (2013.01); *H01M 10/0569* (2013.01); *H01M 12/08* (2013.01); *H01M 2300/0034* (2013.01); *Y02E 60/13* (2013.01)

(58) Field of Classification Search
CPC ... C07C 255/03; C07C 255/14; C07C 242/30; C07C 69/96; H01M 12/08; H01M 10/052; H01M 10/0567; H01M 10/0569; H01M 2300/0034; H01G 11/62; H01G 11/60; H01G 11/64
See application file for complete search history.

(56) References Cited

U.S. PATENT DOCUMENTS

| 4,259,350 A | 3/1981 | Morisawa et al. |
| 4,812,164 A | 3/1989 | Wenger et al. |
| 4,859,229 A | 8/1989 | Wenger et al. |
| 6,063,734 A | 5/2000 | Ogura et al. |
| 6,278,013 B1 | 8/2001 | Bartel et al. |
| 2009/0253048 A1 | 10/2009 | Shima |
| 2009/0291364 A1* | 11/2009 | Koh ............... H01G 9/035 429/188 |

FOREIGN PATENT DOCUMENTS

| EP | 1 890 357 A1 | 2/2008 |
| EP | 2 253 710 A1 | 11/2010 |
| JP | S 55-081837 A | 6/1980 |
| JP | S 63-041466 A | 2/1988 |
| JP | S 63-107967 A | 5/1988 |
| JP | H11-158137 A | 6/1999 |
| JP | 2000-504734 A | 4/2000 |
| JP | 2001 002624 A | 1/2001 |
| JP | 2005-508380 A | 3/2005 |
| JP | 2007-066864 A | 3/2007 |
| JP | 2007-112737 A | 5/2007 |
| JP | 2007112737 * | 5/2007 |
| JP | 2008-504254 A | 2/2008 |
| JP | 2008-522960 A | 7/2008 |
| JP | 2010-027361 A | 2/2010 |
| JP | 2010027361 * | 2/2010 |
| WO | 1997/40009 A1 | 10/1997 |
| WO | 98/35935 A1 | 8/1998 |
| WO | 2001/60797 A1 | 8/2001 |
| WO | 03/040080 A2 | 5/2003 |

(Continued)

OTHER PUBLICATIONS

F. Mares, et al., "Chemistry of 2-(Trifluoromethyl)-2-hydroxy-3,3,3-trifluoropropionitrile", Journal of Organic Chemistry, 1976, vol. 41, No. 9, pp. 1567-1569.
A. G. Dikundwar, et al., "Crystal structures of fluorinated aryl biscarbonates and a biscarbamate: a counterpoise between weak intermolecular interactions and molecular symmetry", CrystEngComm, 2011, vol. 13, pp. 1531-1538.
R. Ramapanicker, et al., "One-pot protection and activation of amino acids using pentafluorophenyl carbonates", Journal of Peptide Science, 2009, vol. 15, No. 2, pp. 849-855.
B. M. Trost, et al., "A Catalytic Asymmetric Wagner—Meerwein Shift", Journal of the American Chemical Society, 2001, vol. 123, No. 29, pp. 7162-7163.

(Continued)

*Primary Examiner* — Ula C Ruddock
*Assistant Examiner* — Thomas H. Parsons

(57) ABSTRACT

Fluorinated carbonyl compounds comprising a triple bond were prepared and their use as solvent additives or solvents in lithium ion batteries, lithium air batteries, lithium sulphur batteries and supercapacitors is described. Preferred compounds contain at least one nitrile or at least one alkynyl group.

13 Claims, No Drawings

(56) References Cited

FOREIGN PATENT DOCUMENTS

WO     2006/009553 A1     1/2006
WO     2006/061146 A1     6/2006

OTHER PUBLICATIONS

S. Kikuchi, et al., "Silver-Catalyzed Carbon Dioxide Incorporation and Rearrangement on Propargylic Derivatives", Bulletin of the Chemical Society of Japan, 2011, vol. 84, No. 7, pp. 698-717.

* cited by examiner

FLUORINATED CARBONYL COMPOUNDS COMPRISING A TRIPLE BOND, METHODS FOR THEIR MANUFACTURE AND USES THEREOF

This application is a U.S. national stage entry under 35 U.S.C. § 371 of International Application No. PCT/EP2013/064504 filed Jul. 9, 2013, which claims priority to European application No. 12176268.6 filed 13 Jul. 2012. The entire contents of these applications are explicitly incorporated herein by this reference.

The present invention concerns fluorinated carbonyl derivatives, methods for the preparation thereof, and their use as solvent or solvent additive for lithium ion batteries and supercapacitors.

Lithium ion batteries, lithium air batteries and lithium sulfur batteries are well-known rechargeable means for storing electric energy. Lithium ion batteries comprise an electrolyte composition containing a solvent, a conductive salt and, often, additives. The solvent is an aprotic organic solvent which serves to dissolve the conductive salt. See, for example, WO 2007/042471 which provides information concerning suitable solvents. Suitable conductive salts are known in the art. $LiPF_6$ is a preferred conductive salt.

Capacitors are widely used devices for storing electrical energy. Among the various types of capacitors are electrochemical capacitors and electrolytic capacitors.

A hybrid supercapacitor is an electrochemical energy storage device that employs two different electrode types, the difference between the electrodes generally being in capacity or composition, and an electrolyte composition.

The optimization of the electrolyte compositions in hybrid supercapacitors still offers a significant potential to improve the performance properties of such systems.

Additives improve the properties of lithium ion batteries, e.g. by extending the lifespan. Fluoroalkyl alkyl carbonates, e.g. fluoromethyl methyl carbonate, and carbamates are known solvent additives for lithium ion batteries. WO 2011/006822 discloses the manufacture of 1-fluoroalkyl (fluoro)alkyl carbonates and carbamates.

The objective of the present invention is to provide improved additives for lithium ion batteries, lithium air batteries, lithium sulphur batteries or supercapacitors. The compounds of the present invention provide advantages like modifying the viscosity or reducing the flammability. Another advantage is the modification of the electrodes under formation of beneficial films. Furthermore, the compounds of the invention lead to a better wettability of materials used in lithium ion batteries such as in particular a separator. The compounds of the invention can suitably assist in the protection against over-charging, for example, by serving as a redox shuttle. Yet another advantage is an increase in stability of the electrolyte composition, e.g. in presence of copper anions, which can be formed by possible degradation of certain current collector materials.

Additionally, the compounds of the present invention may increase energy density of a supercapacitor, their power density or their cycle life.

One aspect of the invention concerns a compound of general formula (I),

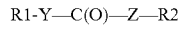

R1—Y—C(O)—Z—R2 wherein Y and Z independently are O, S or NR3; and wherein R3 is H or R4; and wherein R1, R2 and R4 independently are a branched or unbranched alkyl group, a branched or unbranched alkenyl group, an aryl, or an alkylene-aryl, or wherein R1 and R2 together represent an alkylene group; and wherein at least one of the groups R1 and R2 is substituted by at least one fluorine atom and at least one of the groups R1 and R2 comprises at least one triple bond-containing group.

"Triple bond-containing group" is intended to denote a group wherein at least two atoms are bonded together chemically by means of a triple bond. Preferably, the triple-bond containing group is C≡N or C≡C.

The term "alkyl group" is intended to denote an optionally substituted chain of saturated hydrocarbon-based groups, such as, in particular, a C1-C6 alkyl. By way of example, mention may be made of methyl, ethyl, propyl, isopropyl, butyl, t-butyl, pentyl, isopentyl and hexyl.

The term "alkenyl group" is intended to denote an optionally substituted chain of carbon atoms, wherein at least two of the carbon atoms being bonded together chemically by means of a double bond. Examples of alkenyl include ethenyl (vinyl), 1-propenyl, 2-propenyl, 1-butenyl The term "aryl group" is intended to mean an optionally substituted group which derives from an aromatic nucleus such as, in particular, a C6-C10 aromatic nucleus, in particular phenyl or naphthyl.

In a preferred embodiment of the invention Y is O.

In another preferred embodiment of the invention R1 is a branched or unbranched alkyl group substituted by at least one fluorine atom. More preferably, R1 is 1-fluoroethyl.

In another preferred embodiment of the invention Z is O.

In another preferred embodiment of the invention R2 is a branched or unbranched alkyl group substituted by at least one nitrile group. More preferably, R2 is —CH₂CH₂C≡N. Alternatively, R2 preferably is a branched or unbranched alkynyl group, more preferably R2 is —CH₂CH₂C≡CH.

In another preferred embodiment of the invention Y and Z both are O and R1 and R2 together represent an alkylene group. More preferably, Y and Z denote 0 and R1 and R2 together represent —CH₂CH₂—.

In yet another preferred embodiment of the invention the compound of the general formula (I) is CH₃CFHOC(O)OCH₂CH₂CN or CH₃CFHOC(O)OCH₂CH₂C≡CH.

Another aspect of the invention concerns a method for the manufacture of compounds of the general formula (I), R1-Y—C(O)—Z—R2, wherein Y and Z independently are O, S or NR3; and wherein R3 is H or R4; and wherein R1, R2 and R4 independently are a branched or unbranched alkyl group, a branched or unbranched alkenyl group, an aryl, or an alkylene-aryl, or wherein R1 and R2 together represent an alkylene group; and wherein at least one of the groups R1 and R2 is substituted by at least one fluorine atom and at least one of the groups R1 and R2 comprises at least one triple bond-containing group; that comprises a first step of reacting phosgene (ClC(O)Cl) or a phosgene analogue with a compound of the general formula R1-Y—H to form an intermediate of the general formula R1-Y—C(O)X and a second step of reacting the intermediate of the general formula R1-Y—C(O)X with a compound of the general formula H—Z—R2, wherein X denotes a leaving group, preferably chlorine or fluorine.

"Phosgene analogue" is intended to denote a compound that is known in the art as a replacement for phosgene. Preferably, the phosgene analogue is difluorophosgene (FC(O)F), trichloromethyl chloroformate ("diphosgene"), bis (trichloromethyl) carbonate ("triphosgene"), S,S-dimethyl dithio carbonate (DMDTC), carbonyldiimidazole (CDI), or N,N-diphenylurea.

Both steps of the process can be performed in the presence of a base, e.g. in the presence of a tertiary amine, e.g.

triethylamine or pyridine. Alternatively, the steps can be performed in the absence of a base.

Both steps are typically conducted in liquid phase, usually in the presence of a solvent, preferably a polar aprotic solvent. Examples of suitable solvents are acetonitrile, dimethylformamide (DMF), N-methyl-2-pyrrolidone (NMP), tetrahydrofurane, dichloromethane, toluene, $CF_3$-toluene and ionic liquids. Alternatively, the reaction can be performed in the absence of a solvent or—if the reaction is performed in the presence of a base—the base can serve as a solvent.

Yet another aspect of the invention concerns a method for the manufacture of a compound of general formula (I), R1-Y—C(O)—Z—R2, wherein Y is O and Z is O, S or NR3; and wherein R3 is H or R4; and wherein R1 is a branched or unbranched alkyl group substituted by at least one fluorine atom and R2 and R4 independently are a branched or unbranched alkyl group, a branched or unbranched alkenyl group, an aryl group, or an alkylene-aryl group; and wherein at least one of R2 and R4 comprises at least one triple-bond containing group; and
wherein the method of manufacture comprises the step of reacting a fluoroformate of general formula (II), R1OC(O)F, with an alcohol of general formula (III), R2OH, to form a carbonate of general formula (IV), R1OC(O)OR2; or
wherein the method of manufacture comprises the step of reacting a fluoroformate of general formula (II), R1OC(O)F, with an amine of general formula (V), R2R3NH, to form a carbamate of general formula (VI), R1OC(O)NR2R3; or
wherein the method of manufacture comprises the step of reacting a fluoroformate of general formula (II), R1OC(O)F, with a thiol of general formula (VII), R2SH, to form a thiocarbonate of general formula (VIII), R1OC(O)SR2.

The reaction can be performed in the presence of a base, e.g. in the presence of ammonia or a primary, secondary or tertiary amine, e.g. triethylamine or pyridine. Alternatively, the reaction can be performed in the absence of a base.

The process is typically conducted in liquid phase. This process is usually conducted in the presence of a solvent, preferably a polar solvent, more preferably a polar aprotic solvent. Examples of suitable solvents are acetonitrile, dimethylsulfoxide (DMSO), dimethylsulfone ($DMSO_2$), sulfolane, dimethylformamide (DMF), N-methyl-2-pyrrolidone (NMP), acetone, ethyl acetate, tetrahydrofurane, dichloromethane, toluene, $CF_3$-toluene and ionic liquids. Alternatively, the reaction can be performed in the absence of a solvent or—if the reaction is performed in the presence of a base—the base can serve as a solvent.

The reaction temperature during the reaction is not critical. Often, the reaction is exothermic, thus, it may be advisable to cool the reaction mixture. The temperature is preferably equal to or higher than −80° C., more preferably, equal to or higher than −78° C. The upper temperature can be dependent from pressure and boiling point of the starting materials. Often, the temperature is equal to or lower than 85° C. The reaction can be performed in any suitable reactor, e.g. in an autoclave. The reaction can be performed batch wise or continuously.

The resulting reaction mixture can be separated by known methods, e.g. by distillation, precipitation and/or crystallization. If desired, the reaction mixture can be contacted with water to remove water-soluble constituents.

The molar ratio between the alcohol of general structure (III), the amine of general structure (V) or the thioalcohol of general structure (VII) and the fluoroformate of general structure (II) is preferably equal to or greater than 0.9:1. Preferably, it is equal to or lower than 5:1. Very good results are achieved when the ratio is from 0.95:1 to 1.2:1.

In a preferred embodiment of the invention R1 is 1-fluoroethyl and the fluoroformate of general formula (II) used in the method of manufacture is $CH_3CHFC(O)F$.

A process for the manufacture of fluoroformates of the general formula (II) and of the specific example $CH_3CHFC(O)F$ is described in WO 2011/006822.

Another aspect of the present invention concerns the use of a compound of general formula (I), R1-Y—C(O)—Z—R2, wherein Y and Z independently are O, S or NR3; and wherein R3 is H or R4; and wherein R1, R2 and R4 independently are a branched or unbranched alkyl group, a branched or unbranched alkenyl group, an aryl, or an alkylene-aryl, or wherein R1 and R2 together represent an alkylene group; and wherein at least one of the groups R1 and R2 is substituted by at least one fluorine atom; and at least one of the groups R1 and R2 comprises at least one triple bond-containing group; as solvent or as solvent additive for lithium ion batteries, lithium air batteries and lithium sulphur batteries.

Compounds of formula (I) are often applied in solvent compositions or in electrolyte compositions together with at least one suitable solvent known to the expert in the field of lithium ion batteries or supercapacitors. For example, organic carbonates, but also lactones, formamides, pyrrolidinones, oxazolidinones, nitroalkanes, N,N-substituted urethanes, sulfo lane, dialkyl sulfoxides, dialkyl sulfites, acetates, nitriles, acetamides, glycol ethers, dioxolanes, dialkyloxyethanes, trifluoroacetamides, are very suitable as solvents.

Preferably, the aprotic organic solvent is selected from the group of dialkyl carbonates (which are linear) and alkylene carbonates (which are cyclic), ketones, and formamides. Dimethyl formamide, carboxylic acid amides, for example, N,N-dimethyl acetamide and N,N-diethyl acetamide, acetone, acetonitrile, dimethyl carbonate, diethyl carbonate, methyl ethyl carbonate, cyclic alkylene carbonates, e.g. ethylene carbonate, propylene carbonate, and vinylidene carbonate, are suitable solvents.

Fluorosubstituted compounds different from the compounds of formula (I) mentioned above, for example, fluorinated carbonic esters which are selected from the group of fluorosubstituted ethylene carbonates, polyfluorosubstituted dimethyl carbonates, fluorosubstituted ethyl methyl carbonates, and fluorosubstituted diethyl carbonates are other solvents or, preferably, suitable additional additives in the electrolytic compositions. Preferred fluorosubstituted carbonates are monofluoroethylene carbonate, 4,4-difluoro ethylene carbonate, 4,5-difluoro ethylene carbonate, 4-fluoro-4-methyl ethylene carbonate, 4,5-difluoro-4-methyl ethylene carbonate, 4-fluoro-5-methyl ethylene carbonate, 4,4-difluoro-5-methyl ethylene carbonate, 4-(fluoromethyl)-ethylene carbonate, 4-(difluoromethyl)-ethylene carbonate, 4-(trifluoromethyl)-ethylene carbonate, 4-(fluoromethyl)-4-fluoro ethylene carbonate, 4-(fluoromethyl)-5-fluoro ethylene carbonate, 4-fluoro-4,5-dimethyl ethylene carbonate, 4,5-difluoro-4,5-dimethyl ethylene carbonate, and 4,4-difluoro-5,5-dimethyl ethylene carbonate; dimethyl carbonate derivatives including fluoromethyl methyl carbonate, difluoromethyl methyl carbonate, trifluoromethyl methyl carbonate, bis(difluoro)methyl carbonate, and bis(trifluoro)methyl carbonate; ethyl methyl carbonate derivatives including 2-fluoroethyl methyl carbonate, ethyl fluoromethyl carbonate, 2,2-difluoroethyl methyl carbonate, 2-fluoroethyl fluoromethyl carbonate, ethyl difluoromethyl carbonate, 2,2,2-trifluoroethyl methyl carbonate, 2,2-difluoroethyl fluoromethyl carbonate, 2-fluoroethyl difluoromethyl carbonate, and ethyl trifluoromethyl carbonate; and diethyl carbonate derivatives including ethyl (2-fluoroethyl) carbonate, ethyl (2,2-difluoroethyl) carbonate, bis(2-fluoroethyl) carbonate, ethyl (2,2,2-trifluoroethyl) carbonate, 2,2-difluoroethyl 2'-fluoroethyl carbonate, bis(2,2-difluoroethyl) carbonate, 2,2,2-trifluoroethyl 2'-fluoroethyl carbonate, 2,2,2-trifluoroethyl 2',2'-difluoroethyl carbonate, and bis(2,2,2-trifluoroethyl) carbonate, 4-fluoro-4-vinylethylene carbonate, 4-fluoro-5-vinylethylene carbonate, 4,4-difluoro-4-vinylethylene carbonate, 4,5-difluoro-4-vinylethylene carbonate, 4-fluoro-4,5-divinylethylene carbonate, 4,5-difluoro-4,5-divinylethylene carbonate, 4-fluoro-4-phenylethylene carbonate, 4-fluoro-5-phenylethylene carbonate, 4,4-difluoro-5-phenylethylene carbonate, 4,5-difluoro-4-phenylethylene carbonate and 4,5-difluoro-4,5-diphenylethylene carbonate, fluoromethyl phenyl carbonate, 2-fluoroethyl phenyl carbonate, 2,2-difluoroethyl phenyl carbonate and 2,2,2-trifluoroethyl phenyl carbonate, fluoromethyl vinyl carbonate, 2-fluoroethyl vinyl carbonate, 2,2-difluoroethyl vinyl carbonate and 2,2,2-trifluoroethyl vinyl carbonate, fluoromethyl allyl carbonate, 2-fluoroethyl allyl carbonate, 2,2-difluoroethyl allyl carbonate and 2,2,2-trifluoroethyl allyl carbonate.

Other suitable additional additives useful in the electrolyte compositions according to the present invention are those described in WO2007/042471 selected from the group of aromatic compounds consisting of 1-acetoxy-2-fluorobenzene, 1-acetoxy-3-fluorobenzene, 1-acetoxy-4-fluorobenzene, 2-acetoxy-5-fluorobenzyl acetate, 4-acetyl-2,2-difluoro-1,3-benzodioxole, 6-acetyl-2,2,3,3-tetrafluorobenzo-1,4-dioxin, 1-acetyl-3-trifluoromethyl-5-phenylpyrazole, 1-acetyl-5-trifluoromethyl-3-phenylpyrazole, benzotrifluoride, benzoyltrifluoroacetone, 1-benzoyl-3-trifluoromethyl-5-methylpyrazole, 1-benzoyl-5-trifluoromethyl-3-methylpyrazole, 1-benzoyloxy-4-(2,2,2-trifluoroethoxy)benzene, 1-benzoyl-4-trifluoromethylbenzene, 1,4-bis(t-butoxy)tetrafluorobenzene, 2,2-bis(4-methylphenyl)hexafluoropropane, bis(pentafluorophenyl) carbonate, 1,4-bis(1,1,2,2-tetrafluoroethoxy)benzene, 2,4-bis(trifluoromethyl)benzaldehyde, 2,6-bis(trifluoromethyl)benzonitrile, difluoroacetophenone, 2,2-difluorobenzodioxole, 2,2-difluoro-1,3-benzodioxole-4-carbaldehyde, 1-[4-(difluoromethoxy)phenyl]ethanone, 3-(3,5-difluorophenyl)-1-propene, fluorobenzophenone, difluorobenzophenone, 1-(2'-fluoro[1,1'-biphenyl]-4-yl)propan-1-one, 6-fluoro-3,4-dihydro-2H-1-benzothiin-4-one, 4-fluorodiphenyl ether, 5-fluoro-1-indanone, 1-(3-fluoro-4-methoxyphenyl)ethanone, fluorophenylacetonitrile, the group of compounds having an Si—C bond consisting of bis(pentafluorophenyl) dimethylsilane, 1,2-bis[difluoro(methyl)silyl]ethane, N,O-bis(trimethylsilyl)trifluoroacetamide, N-(t-butyldimethylsilyl)-N-methyltrifluoroacetamide, t-butyldimethylsilyl trifluoromethanesulphonate, 2-dimethylamino-1,3-dimethylimidazolium trimethyldifluorosiliconate, diphenyldifluorosilane, the group of compounds having a C=O bond consisting of bis(1,1,1,3,3,3-hexafluoroprop-2-yl) 2-methylenesuccinate, bis(1,1,1,3,3,3-hexafluoroprop-2-yl) maleate, bis(2,2,2-trifluoroethyl) maleate, bis(perfluorooctyl) fumarate, bis(perfluoroisopropyl) ketone, 2,6-bis(2,2,2-trifluoroacetyl)cyclohexanone, butyl 2,2-difluoroacetate, cyclopropyl 4-fluorophenyl ketone, diethyl perfluoroadipate, N,N-diethyl-2,3,3,3-tetrafluoropropionamide, the group of compounds having a C=C bond consisting of allyl 1H,1H-heptafluorobutyl ether, trans-1,2-bis(perfluorohexyl)ethylene, (E)-5,6-difluoroocta-3,7-diene-2-one, the group of amines consisting of N,N-diethyl-1,1,2,3,3,3-hexafluoropropylamine.

The solvent composition or electrolyte composition may also additionally contain benzene, fluorobenzene, toluene, trifluorotoluene, xylene or cyclohexane.

The compounds can be synthesized in a known manner and are also commercially available, for example from ABCR GmbH & Co. KG, Karlsruhe, Germany.

Fluorinated acetamides suitable as solvent or additional solvent additive are for example those described U.S. Pat. No. 6,489,064, namely partially fluorinated amide corresponding to formula $R^1CO—NR^2R^3$ wherein R' is a linear C1-C6 alkyl group in which at least one hydrogen atom is replaced by fluorine, or a branched C3-C6 alkyl group in which at least one hydrogen atom is replaced by fluorine, or a C3-C7 cycloalkyl group optionally substituted one or more times by a linear C1-C6 alkyl group or branched C3-C6 alkyl group or both in which at least one hydrogen atom of the cycloalkyl group or the optional linear or branched alkyl substituent or both is replaced by fluorine, and $R^2$ and $R^3$ independently represent an identical or different linear C1-C6 alkyl group, a branched C3-C6 alkyl group or a C3-C7 cycloalkyl group, or together with the amide nitrogen form a saturated five or six-membered nitrogen-containing ring, or are joined with one or more additional N and/or O atom(s) to form a 4 to 7-membered ring in which the additional N atoms present in the ring are optionally saturated with C1-C3 alkyl groups and the ring carbon atoms may also carry C1-C3 alkyl groups.

Partially fluorinated esters suitable as solvent or additional solvent additive are for example those described in U.S. Pat. No. 6,677,085 partially fluorinated compound derived from a diol corresponding to the formula $R^1CO—O—[CHR^3(CH_2)_m—O]_n—R^2$ wherein $R^1$ is a (C1-C8) alkyl group or a (C3-C8) cycloalkyl group, wherein each of said groups is partially fluorinated or perfluorinated so that at least one hydrogen atom of the group is replaced by fluorine; $R^2$ is a (C1-C8) alkyl carbonyl or (C3-C8) cycloalkyl carbonyl group, wherein said alkylcarbonyl or cycloalkylcarbonyl group may optionally be partially fluorinated or perfluorinated; $R^3$ is a hydrogen atom or a (C1-C8) alkyl or (C3-C8) cycloalkyl group; m is 0, 1, 2 or 3, and n is 1, 2 or 3.

The electrolyte composition, further to the at least one compound of general formula (I), comprises at least one dissolved electrolyte salt. Such salts have the general formula $M_aA_b$. M is a metal cation, and A is an anion. The overall charge of the salt $M_aA_b$ is 0. M is preferably selected from $Li^+$ and $NR_4^+$. Preferred anions are $PF_6^-$, $PO_2F_2^-$, $AsF_6^-$, $BF_4^-$, $ClO_4^-$, $N(CF_3SO_2)_2^-$ and $N(i-C_3F_7SO_2)_2^-$.

Preferably, M is $Li^+$. Especially preferably, M is $Li^+$ and the solution comprises at least one electrolyte salt selected from the group consisting of $LiBF_4$, $LiClO_4$, $LiAsF_6$, $LiPF_6$, $LiPO_2F_2$, $LiN(CF_3SO_2)_2$ and $LiN(i-C_3F_7SO_2)_2$. Lithium bis(oxalato)borate can be applied as an additional additive. The concentration of the electrolyte salt is preferably 1±0.1 molar. Often, the electrolyte composition may comprise $LiPF_6$ and $LiPO_2F_2$.

If $LiPO_2F_2$ is the only electrolyte salt, its concentration in the electrolyte composition is, as mentioned, preferably 1±0.1 molar. If $LiPO_2F_2$ is applied as an additive together with another electrolyte salt, especially together with $LiPF_6$, the concentration of $LiPO_2F_2$ in the electrolyte composition preferably is equal to or greater than 0.1% by weight, more preferably equal to or greater than 0.5% by weight; preferably, its concentration is equal to or lower than 10% by weight, more preferably, equal to or lower than 5% by weight when the total electrolyte composition including electrolyte salt, solvent and additives is set as 100% by weight.

Another aspect of the present invention is an electrolytic composition comprising at least one compound of the general structure (I),

R1—Y—C(O)—Z—R2 wherein Y and Z independently are O, S or NR3; and wherein R3 is H or R4; and wherein R1, R2 and R4 independently are a branched or unbranched alkyl group, a branched or unbranched alkenyl group, an aryl, or an alkylene-aryl, or wherein R1 and R2 together represent an alkylene group; and wherein at least one of the groups R1 and R2 is substituted by at least one fluorine atom; and at least one of the groups R1 and R2 comprises at least one triple bond-containing group.

Preferably, the electrolyte composition comprises at least one compound of the general formula (I), at least one electrolyte salt and at least one solvent and optionally at least one further additive. Preferred compounds of the general formula (I), preferred electrolyte salts, preferred solvents and preferred additives are those given above.

The compound of formula (I) is contained in the compositions in an amount greater than 0 and preferably equal to or lower than 10% by weight of the total composition. The amount of electrolyte salt is preferably in the range 1±0.1 molar.

The compounds of formula (I) can be introduced into the electrolyte composition separately or in the form of a mixture with other compounds, e.g. as a mixture with one or more solvents used in the electrolyte composition or together with the electrolyte salt or together with other additives.

Still another aspect of the present invention are lithium ion batteries, lithium air batteries and lithium sulfur batteries comprising a solvent composition as outlined above or an electrolyte composition as outlined above.

In another aspect of the invention, the lithium ion batteries comprises an anode, preferably an anode made from carbon comprising a copper foil, a cathode, preferably a cathode made from lithium metal oxides comprising an aluminum foil, a separator, preferably a separator made from an insulating polymer, and a solvent composition or an electrolyte composition as described above. The foils used for anode and cathode are also called current collectors.

Yet another aspect of the present invention are supercapacitors or hybrid supercapacitors comprising a solvent composition as outlined above or an electrolyte composition as outlined above.

Should the disclosure of any patents, patent applications, and publications which are incorporated herein by reference conflict with the description of the present application to the extent that it may render a term unclear, the present description shall take precedence.

The invention will now be further described in examples without intending to limit it.

EXAMPLES

Example 1: Synthesis of 2-Cyanoethyl 1'-Fluoroethyl Carbonate

In a 2.5 L reactor made of Perfluoroalkoxy (PFA) equipped with a mechanical stirrer and a reflux condenser 987 g (8.1 mol) 1-fluoroethyl fluoroformate was cooled to 4° C. Over a period of 2.25 h 841 g of a mixture of pyridine and 3-hydroxypropionitrile (226 g pyridine (2.9 mol), 615 g 3-hydroxypropionitrile (8.5 mol)) was added to the 1-fluoroethyl fluoroformate under stirring and cooling. The reaction temperature was kept below 60° C. After an additional 4 h of stirring, the reaction was complete. The mixture was washed with aqueous citric acid three times (500 mL, 300 mL, 200 mL) and dried with molecular sieve. After filtration 2-cyanoethyl 1'-fluoroethyl carbonate is obtained as a slightly yellowish liquid (1023 g, 6.3 mol).

$^1$H NMR (500 MHz, chloroform-d) δ [ppm]=1.47-1.70, (ddd, J=21 Hz, 6 Hz, 3 Hz, 3H) 2.79 (td, J=6 Hz, 1 Hz, 2H), 2H), 4.28-4.49 (m, 2H), 6.34 (dqd, J=56 Hz, 5 Hz, 3 Hz, 1H).

$^{13}$C NMR (125 MHz, chloroform-d) δ [ppm]=17.8, 19.4 (d, J=23 Hz), 62.3, 103.7, 105.5, 116.2, 152.6.

$^{19}$F NMR (471 MHz, chloroform-d) δ [ppm]=121.35 (dq, J=56 Hz, 21 Hz).

Example 2: Synthesis of 1-Fluoroethyl Propargyl Carbonate

A 2.5 l PFA-reactor equipped with a temperated double mantle, a reflux condenser and a mechanical stirrer was charged with 1190 g 1-fluoroethyl fluoroformate. After cooling to 3° C., a mixture of 284 g pyridine and 591 g propargyl alcohol was slowly added over a period of 2 hours. The reaction temperature was kept below 50° C. After cooling to r.t., the mixture was washed with a 30% aqueous citric acid solution three times (200 ml, 125 ml, 75 ml). The product was obtained as a colourless liquid in a yield of 1164 g (74%) with a purity>96% (GC assay).

The products can optionally be further purified, e.g. by distillation, crystallization, or precipitation.

The invention claimed is:

1. A compound of general formula (I),

R1—O—C(O)—O—R2 wherein R1 is a branched or unbranched alkyl group substituted by at least one fluorine atom;
wherein R2 is a branched or unbranched alkyl group substituted by at least one nitrile group or an unbranched alkynyl group.

2. The compound according to claim 1 wherein the compound is CH$_3$CFHOC(O)OCH$_2$CH$_2$CN, CH$_3$CFHOC(O)OCH$_2$CH$_2$C≡CH, or 1-fluoroethyl propargyl carbonate.

3. A method for the manufacture of a compound according to claim 1 of general formula (I),

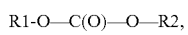

R1—O—C(O)—O—R2, wherein R1 is a branched or unbranched alkyl group substituted by at least one fluorine atom;
wherein R2 is a branched or unbranched alkyl group substituted by at least one nitrile group or an unbranched alkynyl group;
the method comprising a first step of reacting phosgene or a phosgene analogue with a compound of the general formula R1-O—H to form an intermediate of the general formula R1-O—C(O)X and a second step of reacting the intermediate of the general formula R1-O—C(O)X with a compound of the general formula H—O—R2, wherein X is a leaving group.

4. The method according to claim 3, wherein the leaving group is chlorine or fluorine.

5. A solvent composition for lithium ion batteries, lithium air batteries, lithium sulfur batteries, supercapacitors or hybrid supercapacitors, the solvent composition comprising at least one solvent useful for lithium ion batteries and at least one compound according to claim 1.

6. An electrolyte composition for lithium ion batteries, lithium ail batteries, lithium sulfur batteries, supercapacitors or hybrid supercapacitors, the electrolyte composition comprising at least one compound according to claim 1, at least one solvent useful for lithium ion batteries or supercapacitors and at least one electrolyte salt.

7. A lithium ion battery, a lithium air battery or a lithium sulfur battery containing at least one compound according to claim 1.

8. A supercapacitor or hybrid supercapacitor containing at least one compound according to claim 1.

9. The compound according to claim 1, wherein R1 is 1-fluoroethyl.

10. The compound according to claim 1, wherein R2 is —CH2CH2C≡N.

11. The compound according to claim 1, wherein R2 is —CH2CH2C≡CH.

12. A method for the manufacture of a compound of general formula (I),

R1-O—C(O)—O—R2 wherein R1 is a branched or unbranched alkyl group substituted by at least one fluorine atom; and wherein R2 is a branched or unbranched alkyl group substituted by at least one nitrile group or an unbranched alkynyl group; and wherein the method of manufacture comprises the step of reacting a fluoroformate of general formula II, R1OC(O)F, with an alcohol of general formula III, R2OH, to form a carbonate of general formula IV, R1OC(O)OR2.

13. A solvent additive or solvent for lithium ion batteries, lithium air batteries, lithium sulphur batteries, supercapacitors or hybrid supercapacitors comprising a compound of general formula (I),

R1-O—C(O)—O—R2 wherein R1 is a branched or unbranched alkyl group substituted by at least one fluorine atom;

wherein R2 is a branched or unbranched alkyl group substituted by at least one nitrile group or an unbranched alkynyl group.

* * * * *